United States Patent [19]

Colman et al.

[11] 4,448,768

[45] May 15, 1984

[54] PROTECTION AGAINST DENTAL CARIES

[75] Inventors: Geoffrey Colman, Sevenoaks; Roy R. B. Russell, Bromley, both of England

[73] Assignee: The Secretary of State for Social Services in Her Britannic Majesty's Government of the United Kingdom of Great Britain and Northern Ireland, London, England

[21] Appl. No.: 303,539

[22] Filed: Sep. 18, 1981

Related U.S. Application Data

[63] Continuation-in-part of Ser. No. 68,443, Aug. 21, 1979, abandoned.

[30] Foreign Application Priority Data

Sep. 1, 1978 [GB] United Kingdom ............... 35383/78

[51] Int. Cl.³ .................... A61K 39/09; C12P 21/00
[52] U.S. Cl. ....................................... 424/92; 435/68; 424/50; 424/49; 424/88; 260/112 R
[58] Field of Search ....................... 424/85, 92, 87, 50; 435/253, 68; 260/112 R

[56] References Cited

PUBLICATIONS

Russell, M., et al., Arch. Oral. Biol., vol. 23, pp. 7–15, 1978.

Iacono, V., et al., Injection and Immunity, vol. 11, pp. 117–128, 1975.

*Primary Examiner*—Blondel Hazel
*Attorney, Agent, or Firm*—Stevens, Davis, Miller & Mosher

[57] ABSTRACT

An antigenic protein, termed antigen A, present on the cell walls and in cultures of *Streptococcus mutans*, especially genetic group I (serotypes c, e and f) is separated from other antigenic proteins, notably those which cross-react with heart tissue, to give an antigenic preparation which may be used as a vaccine or to raise antibodies for use in protecting against dental caries.

Antigen A is one of two major antigenic proteins remaining on cell walls of *S. mutans* genetic group I after extraction with a boiling 10 g/l liter aqueous solution of sodium dodecyl sulphate for 20 minutes. It has a molecular weight of about 29,000, an isoelectric point of 4.1 to 4.5. Its amino-acid analysis is also given.

The antigen also occurs in the culture filtrate and/or cell extract and may be readily purified from these sources by, for example fractional ammonium sulphate precipitation and/or affinity chromatography on immobilized antibody.

4 Claims, 2 Drawing Figures

PROTECTION AGAINST DENTAL CARIES

This application is a continuation-in-part of Ser. No. 68,443, filed Aug. 21, 1979, now abandoned.

The invention relates to antigenic protein preparations for use in vaccines to reduce the incidence of dental caries, to methods of preparing said preparations and to formulations incorporating said preparations or antibodies thereto.

Dental caries is widely recognised as being caused by acid generated by bacteria colonising the surface of the teeth the major bacterial species involved being that known as *Streptococcus mutans*. This recognition has led to numerous attempts to prevent, or at least reduce, the incidence of dental caries by immunisation with whole cells or cell components of *S.mutans*. Thus experiments have been described (Bowen et al, British Dental Journal, Vol 139, 1975, pp 45-48; Cohen et al, British Dental Journal Vol 147, 1979 pp 9-14) wherein the incidence of dental caries in monkeys was reduced by immunisation with either whole cells or the cell-wall rich material deposited from disintegrated cells by centrifugation. (Immunisation with glucosyltransferase enzyme preparations produced no protection). Although such immunisation has been shown to generate an immune response producing antibodies to the *S.mutans* bacteria, the route by which said antibodies reach the oral colonies is uncertain. Protection has been observed following immunisation submucosally in the mouth or subcutaneously in the leg. An alternative though probably more expensive approach involves topical application of antibody preparations for example bovine milk containing antibodies to *S.mutans* antigens (UK Pat. No. 1,505,513).

Whilst immunisation with whole cell or cell-wall preparations of *S.mutans* appears to confer protection, it may also be attended by certain hazards, especially when live whole cells are used. Streptococci are known to be implicated in certain diseases, for example rheumatic heart diseases and immunisation with whole cells of even uncharacterised cell components may give rise to undesirable side effects. Thus for maximum safety, as well as maximum efficiency, the vaccine should contain only the specific antigen or antigens necessary to confer protection against dental caries.

We have now identified two antigenic proteins (hereinafter termed antigens A and B) which are present in the above described cell wall preparations and which appear to be involved in protection against dental caries.

Antigen B has been demonstrated to stimulate antibodies which react with human heart tissue (Hughes, Pathogenic Streptococci, 1979, pp 222-223, edited by M. T. Parker, Reedbooks, Chertsey, England). The possibility that vaccination with preparations containing antigen B would induce a heart-damaging autoimmune response means that antigen B as presently characterised will be unacceptable in a vaccine.

Accordingly the invention provides an antigen preparation containing antigen A (as hereinafter defined) substantially free from other antigenic proteins derived from *Streptococcus mutans*. The invention further provides a pharmacological preparation comprising such an antigen preparation or antibodies thereto in a pharmaceutically acceptable carrier. The term pharmacological preparation as used herein covers both prophylactic agents, for example vaccines, and agents for use following infection to reduce resulting damage.

Antigen A is that antigenic protein remaining on the cell walls of *Streptococcus mutans* serotype c (as described by Bratthall, Odontologisk Revy 20, 1969, 231-243) of which the strain NCTC 10449 is an example, after extraction of the cell with 10 grm/l sodium dodecyl sulphate (SDS) in water for 1 hour at room temperature or 20 minutes with boiling water which has a molecular weight of about 29,000±3,000 and an isoelectric point of 4.1 to 4.5. Substantially identical proteins are found in other strains of *S.mutans* genetic group I (Coykendall. J.Gen Microbiol Vol 83 pp 327-338) including serotypes e and f, for example the strains described by Russell RRB, Microbios Letters, Vol 2 (1976) pp 55-59. Antigenically related proteins are found in strains of other genetic groups, for example serotype b. The present invention includes such antigenically related proteins and the term "Antigen A" as used in this description and accompanying claims should be understood to include them. Thus the invention is not restricted to any particular strain or strains.

Antigen A cannot readily be separated from the SDS extracted cell walls, but immunisation of rabbits with the extracted cell walls, yields antisera to two proteins (termed Antigens A and B) which may thereby be detected in and separated from whole cell extracts or cell-free culture filtrates. The antigen is thus conveniently produced from culture filtrates or from whole cultures following cell disruption.

According to another aspect of the invention, therefore, a process for preparing antigen A (as hereinbefore described) comprises growing bacteria of the species *Streptococcus mutans*, in a suitable culture medium, removing at least the cell walls from the resulting culture, to leave a protein solution and separating the Antigen A from said protein solution.

The culture medium may be any conventional medium for *S.mutans* such as Todd-Hewitt broth (Todd E. W. & Hewitt L. F., J.Path & Bacteriol, 35, 1932, pp 973-974), tryptone/yeast extract or a chemically defined medium. For ease of subsequent purification a chemically defined medium is preferred. Antigen A is released into the growth medium at all stages of the culture. Advantageously cell are harvested at early stationary phase (typically 15-25 hours at 37° C.). The cells may also be grown in continuous culture.

The protein solution may comprise merely culture filtrate obtained by removing whole cells or a cell extract freed from cell walls and debris or may be a mixture of these produced by disrupting the cells of a whole culture and subsequently removing cell walls and debris. The cell walls may be removed, either as whole cells or as fragments following disintegration, by conventional techniques such as centrifugation or filtration.

Antigen A may be separated from the protein solution by conventional techniques, for example by ammonium sulphate precipitation followed by chromatography. The precipitation with ammonium sulphate may be carried out in a single stage preferably to 65% saturation, but is advantageously conducted in two stages to 45% and 65% saturation. The precipitate from the first stage contains only a minor proportion of antigen A whilst that from the second stage contains the bulk of the antigen A and a lower proportion of other proteins, notably antigen B. The antigen A may be separated chromatographically from either the second stage precipitate only or from both precipitates depending on the economics of the process.

The chromatographic separation may be performed on any suitable conventional media such as a cross-linked dextran or agarose gel or dextran-substituted triazine dye immobilised on agarose gel. A particularly suitable material is diethylamino-ethyl cross-linked dextran. The proteins may be eluted by conventional pH or ionic gradients, preferably a sodium chloride ionic gradient when Antigen A is eluted at 0.1 to 0.2 molar Na Cl. Alternatively affinity chromatography or immuno adsorbent chromatography may be applied either to the ammonium sulphate precipitate or the crude cell extract and/or supernatant.

Preferably the antigen A is separated from the protein solution by affinity chromatography on immobilised anti-antigen A antibodies. The antibodies may typically be immunoglobulin G (IgG) antibodies raised in a suitable animal such as rabbit and may be immobilised on a conventional support such as cross-linked agarose beads following cyanogen bromide activation.

The purified antigen A preparation may be formulated into a vaccine with conventional pharmaceutically acceptable carriers including adjuvants (for example aluminium hydroxide), stabilising agents and bacteriostats. The vaccine may contain protein from one or several strains of S.mutans and may be administered to man or other mammals subcutaneously, intramuscularly, intravenously or submucosally typically at doses of 1–50, especially about 10, $\mu$g per Kg body weight. Multiple injections may be required to generate sufficient antibody response. Protection may also be elicited by immunisation via an oral route, eg, by swallowing a capsule containing the antigen.

According to an alternative aspect of the invention, a preparation for the prevention or control of dental caries in mammals comprises antibodies to antigen A in a pharmaceutically acceptable vehicle. The preparation may be an injectable preparation or may be a formulation suitable for topical application, for example a toothpaste or mouth-wash.

It will be appreciated that the action of all the products according to the invention is due to antibodies to antigen A, whether included in the product as administered or generated by the immune response of the subject. The action of these antibodies in preventing dental caries is not fully understood but such understanding is not essential to the practice of the invention. It is possible that they affect the metabolism of the bacterial cells preventing the formation either of glucan or acid. It should, however, be understood that the invention is in no way limited by a specific theory of the mode of action of the materials. Similarly the invention is not limited to the specific strains of Streptococcus mutans listed above or used in the following examples.

Typical processes and products in accordance with the invention will now be described by way of example with reference to the accompanying drawings in which.

PRODUCTION OF ANTISERUM TO SDS EXTRACTED CELL WALLS

Figure 1:
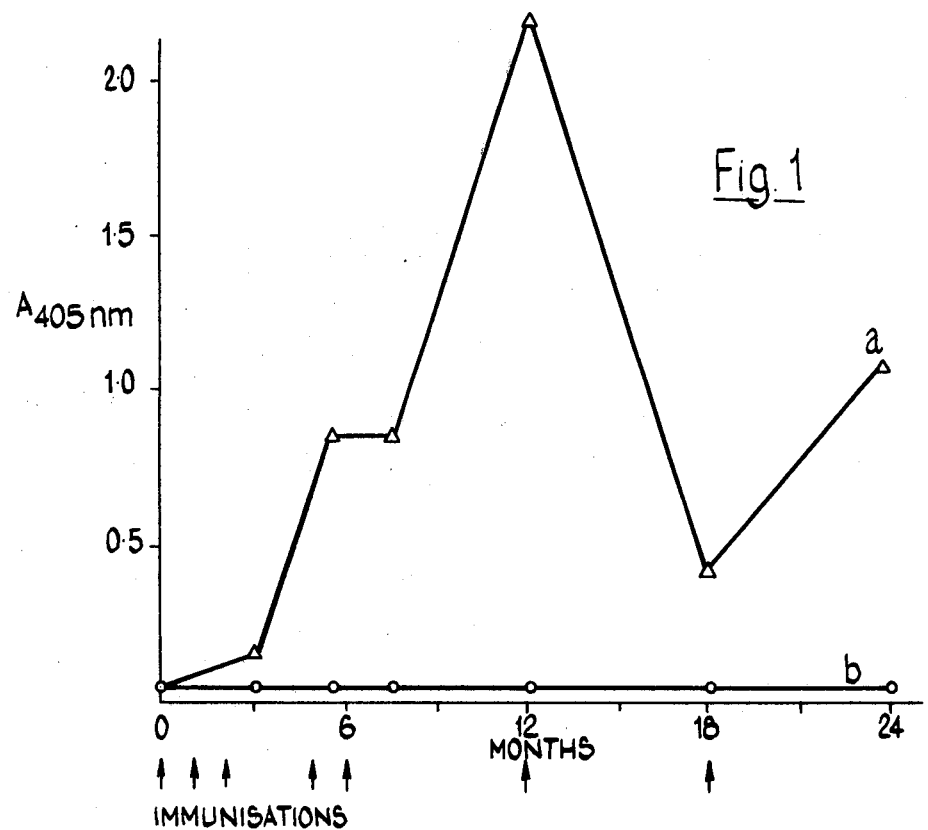
FIG. 1 shows IgG responses to antigen A in immunised (curve a) and control (curve b) animals.

Streptococcus mutans, of the well known strain Ingbritt was used. This strain has been described by Krasse. B; Archs. Oral Biol; 11 pp 429–436 and is classified as genetic type 1 by the system of Coykendal (J.Gen. Microbiol 83, 1974, 327–338) and serotype c according to Bratthall (Odont.Revy 20, 1969, 231–243) and deposited with the NCIB, Aberdeen, Scotland as NCIB 11516.

The bacteria were grown in Todd-Hewitt broth (as described by Todd E. W and Hewitt L. F., J. Path and Bacteriol, Vol 35, 1932 pp 973–974) until the stationary phase was reached (16 hours). The cells were then harvested by centrifugation and suspended in the sodium dedecyl sulphate (SDS) solubilising buffer of Laemmli (Nature 227, 1970, pp 680–685) in a boiling water bath for 20 minutes. The cells were then washed extensively in water by centrifugation, freeze-dried and resuspended in water at a concentration of 10 mg/ml. A rabbit was immunised with these SDS-extracted cells, 1 ml plus 0.1 Aluminium hydroxide adjuvant being injected intramuscularly at day 0, 21 and 48. On day 55 the rabbit was exsanguinated by cardiac puncture.

Similar results were obtained when the cells were extracted with a 10 grm per liter aqueous solution of SDS with boiling for 20 minutes or for 1 hour at room temperature.

CHARACTERISATION OF ANTIGENS A AND B

Antiserum prepared as above was tested by immunodiffusion against cell components of Ingbritt (in the form of a sonicated extract of whole cells) as well as proteins from a culture filtrate of Ingbritt which had been concentrated by ammonium sulphate precipitation. Two precipitin lines were observed, and these were antigenically identical between sonicate and supernatant. Treatment of either antigen preparation with a non-specific proteolytic enzyme Pronase, (Sigma Chemical Co) resulted in no precipitin lines being subsequently formed, demonstrating the protein nature of the antigens.

When an antiserum to SDS extracted cell walls of S.mutans serotype c was tested against the cell sonicate and culture filtrate by the more sensitive technique of crossed immunoelectrophoresis, still only two antigen-/antibody precipitin reactions could be detected.

The same two antigens could be detected when another serotype c strain, available from the National Collection of Type Cultures, Colindale, England as NCTC 10449, was extracted and used to raise antiserum as described above.

Information on the physical properties of the two antigens was obtained by crossed immunoelectrophoresis in which the first dimension separation was by isoelectric focussing in polyacrylamide gel (to separate proteins according to their charge differences) or by SDS-polyacrylamide gel electrophoresis (to separate proteins according to their molecular weight). The results obtained indicated that antigen A had an isoelectric point of 4.3 and a molecular weight of 29,000±3,000 while antigen B had isoelectric point 5.4 and molecular weight of near 200,000. The more accurate technique of SDS-polyacrylamide gradient gel electrophoresis confirmed the value of 29,000 for A, and gave a value of 190,000 for B. The marker proteins used as molecular weight standards were rabbit myosin, 200,000; $\beta$-galactosidase, 116,000; phosphorylase A, 94,000; bovine serum albumin, 68,000; ovalbumen, 43,000; chymotrypsinogen A, 25,700. The value for B is as yet provisional, as differential staining methods indicated B to contain some carbohydrate and glycoproteins are known to show anomalous migration in gel electrophoresis.

The antiserum raised against SDS-extracted cells of Ingbritt was used to demonstrate that antigens identical to A and B were produced by 6 other strains of serotype c (including FW293, C67-1 GS-5 and OMZ-70, as described by Russell, RRB, Microbios Letters, Vol 2 (1976), pp 55-59) and also by representative strains of serotypes e (strain P4) and f (strain 151). These latter two serotypes are in the same genetic group as serotype c (ie Genetic Group I of Coykendall, for which the name *S.mutans* Clarke has been proposed (Coykendall, 1977, Int, J. Syst.Bacteriol 27, pp 26-30) and have been shown to be closely related antigenically (Bratthall, et al J.dent Res 55A, 1976, pp 60-64; Perch et al, Acta path microbiol scand Sec B82, 1974, pp 357-370) and have similar protein compositions (Russell, Microbios Letters 2, 1976 pp 55-59). Serotype b strains contain an antigen cross-reacting with antigen A, while antigens cross-reacting with antigen B have been observed in serotypes a,d and g and strains of *S.sanguis*.

1a. PREPARATION OF PURIFIED ANTIGEN A

Following detection of proteins A and B in culture filtrates, further experiments showed that both antigens are excreted throughout the growth cycle in either Todd-Hewitt broth, tryptone/yeast/extract, or the chemically defined (CD) medium of Janda and Kuramitsu (Infect. Immun 14, 1976, pp 191-202). As the CD medium contains fewest components likely to interfere with purification procedures it was selected for use. *S.mutans* strain Ingbritt was grown in CD medium to early stationary phase, and the cells removed by centrifugation followed by filtration through glass fibre. If it is desired to prepare pure antigen B, the filtrate should be passed down a chromatography column containing the insoluble glucose polymer mutan and polyacrylamide gel beads (BioGel P2) prepared as described by McCabe and Smith (Infect. Immun, 1977, 16: 760-765) in order to remove the glucosyltransferase enzymes which otherwise tend to co-purify with antigen B. Solid ammonium sulphate was slowly added so as to give a 45% saturated solution, and the precipitate which formed overnight at 4° C. was collected by centrifugation. Preliminary experiments had shown that antigen B was maximally precipitated at 45% saturated ammonium sulphate, while antigen A was maximally precipitated at 65%. Further ammonium sulphate was therefore added to bring the culture filtrate to 65% of saturation, and the precipitate again collected. Both fractions were dialysed against 50 mM Tris HCl buffer (pH 7.5), which buffer was used throughout the purification, prior to the next step which was chromatograhy on DEAE cross-linked dextran (DEAE Sephadex A25—Trade Mark). Samples were applied to separate columns which had previously been equilibrated with Tris buffer. The columns were eluted by passing down one volume of Tris buffer before applying a linear gradient of 0 to 0.3 M NaCl in Tris. Sequential fractions were collected and analysed by SDS-polyacrylamide slab gel electrophoresis and by fused rocket immunoelectrophoresis against the antiserum prepared against SDS-extracted cells.

Antigen B (from 45% ammonium sulphate) eluted at approximately 0.8 M NaCl while Antigen A eluted at approximately 0.13 M NaCl. In each case the antigenic proteins were estimated to be about 90% pure. Antigen-containing fractions were pooled, dialysed against the Tris buffer and concentrated by ultrafiltration. Each partially-purified antien was then applied to a column of agarose gel (Sepharose CL-6B—Trade Mark), and eluted with Tris buffer. Fractions were again collected and analysed for antigens and protein composition.

The above procedure yielded preparations of proteins A and B which were apparently pure by the criteria of SDS-polyacrylamide gel electrophoresis and isoelectric focussing in polyacrylamide gel.

When these preparations of antigens A and B were injected into rabbits with adjuvant, following an immunisation schedule identical to that described above for SDS-extracted cells, monospecific antisera were produced which when testted against crude antigen preparations by precipitation-in-gel techniques precipitated only the homologous antigen.

The monospecific antisera raised against antigens A and B can be used for the immunosorbent affinity chromatography purification of the antigens. In a typical preparation the immunoglobulin G fraction of the serum was coupled to cross-linked agarose beads (CnBr-activated Sepharose, Pharmacia) by the manufacturers recommended procedures. Concentrated culture filtrate from *S.mutans* strains Ingbritt in 0.05 M Tris/HCl buffer pH 7.5 containing 1% Triton X-100 was passed down the column. The column was then washed with several volumes of the Tris buffer before eluting with either Tris buffer containing 3 M sodium thiocyanate or 0.1 M glycine/HCl buffer pH 2.8 (though other eluting agents may prove equally satisfactory). The procedure yields pure preparations of the required antigen. Should any leakage of IgG from the column occur, this can readily be separated from the antigen by ion-exchange chromatography as already described.

The amino acid composition of the affinity-purified antigen was determined after hydrolysis for 48 h at 105° C. in 6 N HCl and is shown in Table 1.

TABLE 1

| Amino acid composition of protein hydrolysates | | |
|---|---|---|
| | Residues per 1000 total residues | |
| | antigen A | antigen B |
| Aspartic acid | 101 | 103 |
| Threonine | 56 | 60 |
| Serine | 91 | 61 |
| Glutamic acid | 106 | 111 |
| Proline | 65 | 44 |
| Glycine | 190 | 212 |
| Alanine | 89 | 117 |
| Cystine | — | — |
| Valine | 53 | 58 |
| Methionine | — | — |
| Isoleucine | 38 | 38 |
| Leucine | 61 | 53 |
| Phenylalanine | 28 | 25 |
| Tyrosine | — | 10 |
| Histidine | 50 | 18 |
| Lysine | 46 | 64 |
| Arginine | 27 | 26 |
| Amino sugar | — | 4 |

1b. PREPARATION OF PURIFIED ANTIGEN A

*S.mutans* strain Ingbritt was grown for 18 hr at 37° C. on a semi-defined medium containing casamino acids. After this time the cells were removed by centrifugation followed by filtration through glass fibre. Sodium azide (0.02%) and phenylmethylsulphonyl fluoride (1 mM) were then added to the filtrates. In order to remove the glucosyltransferase enzymes the filtrates were then passed down a column of immobilised mutan prepared as described in McCabe et al, Infect. Immun, 1977, 16, 760. After the proteins dissolved in the collected fractions had been concentrated by precipitation with, optionally, 65% saturated ammonium sulphate, followed by dialysis against 50 mM Tris HCl buffer (pH 7.5), they were passed down an immunosorbent column of immobilised antibody of antigen A. (The immunosorbent column was prepared by coupling the immunoglobulin fraction of the monospecific antiserum raised against antigen A to cross-linked agarose beads (CnBr activated Sepharose-Pharmacia) by the manufacturer's recommended procedures.)

The column was then washed with at least 10 column volumes of 50 mM Tris HCl (pH 7.5) and eluted with 3 M sodium thiocyanate in 50 mM Tris HCl (pH 7.5), or 0.1 M glycine/HCl (pH 2.5). The eluted fractions were collected, dialysed against 50 mM Tris HCl and finally subjected to ion-exchange chromatography on DEAE cross-linked dextran (DEAE Sephadex A25—Trade Mark) by the procedure described in *J. Gen. Microbiol*, 1979, 114, 109. The purity of the final product was examined by crossed immunoelectrophoresis against serum raised against *S.mutans* whole cells.

1c. PREPARATION OF PURIFIED ANTIGEN A

*S.mutans* strain Ingbritt was grown for 18 hr at 37° C. on a semi-defined medium containing casamino acids. After this time the cells were collected by centrifugation and then stirred in a 1% aq solution of sodium dodecyl sulphate (10 g wet cells in 100 ml solution) for 2 hr. The cells were washed extensively by centrifugation (to remove SDS) and then freeze-dried. (As an alternative to SDS washing, the cells may be washed in 6 M guanidine HCl). The freeze dried cells were suspended (at a concentration of 20 mg/ml) in 50 mM Tris—HCl (pH 7.5) buffer containing 200 μg/ml Mutanolysin enzyme M-1 (supplied by Yokogawa) and 1 mM phenylmethylsulphonyl fluoride. The suspension was stirred for 3 hr at 37° C. and then centrifuged to remove the solid material. The solubilised material was then purified by application to an immunosorbent column of immobilised antibody to antigen A as described in Examples 1a and 1b above.

As above the purity of the final product was examined by crossed immunoelectrophoresis against serum raised against *S.mutans* whole cells.

ASSESSMENT OF ANTIGENIC AND PROTECTIVE PROPERTIES

Antigens A and B are exposed on the surface of the bacterium and function as immunogens. Thus experiments involving immunisation of several dozen rabbits and monkeys have shown that antibody responses to antigens A and B are markedly stronger than to other antigens. This effect is even more marked when animals are immunised with cell wall-enriched preparations. As described above, SDS-extracted walls elicit antibodies to only A and B, while walls subjected to less rigorous extraction still give their most powerful responses to A and B while weaker responses to not more than two other antigens have been observed.

Antibodies may be detected by the conventional techniques of crossed immunoelectrophoresis or reversed-rocket line electrophoresis.

Quantitation of antibody responses has been performed by enzyme-linked immunosorbent assay (ELISA), following the microplate technique of Voller, Bidwell and Bartlett (1977, Flowline Publications). Plastic Microtiter trays were coated with immunoaffinity purified antigens A or B at concentrations of approximately 1 μg/ml.

Assay of the amount of monkey antibody binding to antigen was achieved by incubating with anti-human IgG conjugated to alkaline phosphatase (Don Whitley Ltd). Results have been expressed either as an endpoint titre (ie the final well of a dilution series which shows a definite colour), or by measuring the absorbance at 405 nm yielded by a serum sample at a particular dilution.

IMMUNOGENICITY OF WHOLE CELLS

Several experiments in which monkeys have been successfully immunised with whole cells of *S.mutans* have been described as cited above (Bowen et al, Brit.-Dent.J. 1975 and Cohen et al Brit.Dent. J 1979) with the reduction in caries being 50% or greater. In a representative experiment 4 experimental and 2 control animals were treated similarly with killed whole cells (Group 14 of Cohen et al, British Dental Journal Vol 147, 1979 pp 9–14). Injections were given at months 0, 2, 5, 6, 12 and 18. The mean antibody (IgG) levels in experimental and control groups are shown in FIG. 1. The level of antibodies after 12 months to antigen A was at least 30-fold that in controls, though this level drops between boosts. It must be stressed that it is unlikely that so many injections are essential for protection, but this aspect of the invention has not been explored.

Four years after the start of the experiment the control animals had a mean number of 5 carious lesions in their permanent teeth, while the immunised animals had a mean of 2 lesions.

From these results it can be seen that there is an apparent correlation between levels of antibody to antigen A and protection from dental caries. Antibodies to antigen A occur only rarely and at low levels in non-immunised subjects. Such "natural antibody" to antigen B has also been observed in some cases. It is not known when these antibodies arose, or whether they are due to antigenic stimulation by *S.mutans* on the teeth, systemic infection by *S.mutans*, or cross-reactivity of antigens or other bacteria to which the animal has an immune response.

In another experiment a group of 8 monkeys were immunised with whole cells plus aluminium hydroxide adjuvant by subcutaneous injection into the leg (Group 11 of Cohen et al, British Dental Journal, as above) and compared with 8 control animals. In this group levels of antibody to antigen A were elevated in all control animals, the mean titre being 1/520. (Note that due to variations in procedure, it is not possible to compare the titres presented here for different groups). The mean titre in animals immunised with whole bacteria however, 6 months after a booster injection, was 1/2830—more than 5 times the level in controls. Antibodies to antigen B were also present in immunised animals. A 55% reduction in caries was observed as between immunised and control animals.

IMMUNOGENICITY OF BROKEN CELL WALLS

Immunisation with broken cell walls of strain Ingbritt as described by Bowen et al (British Dental Journal 1975, pp 45–58) has been shown to confer protection against subsequent challenge by that strain. Immunisation with trypsinised cell walls does not confer protection indicating that a protein is involved in the protective process.

Sera were collected from four experimental monkeys immunised with a cell wall preparation of the Ingbritt strain and challenged with the same strain as described for Group C by Bowen et al. Five control monkeys were similarly challenged without immunisation.

Control animals had titres of antibody to antigen A of 1/20 (3 animals), 1/80 (1 animal) and 1/1280 (1 animal) while the immunised and protected animals had titres between 1/80 and 1/640 with a mean value of 1/220. These values were obtained from serum samples taken 20 months after the last booster injection. Levels would, of course, be much higher just after a boost.

Five years after the start of the experiment the total number of carious lesions in the four experimental animals was 4. In the 5 control animals the total number of lesions was 64 and the number bore an inverse relation to the level of antibodies in the serum, with the two control animals that did not show any antibody response exhibiting rampant caries.

Nine years after the start of the experiment there are 5 surviving animals, two of the immunised group and 2 controls having died. The 3 surviving control animals have all succumbed to rampant caries, having 56, 69 and 93 decayed surfaces respectively. A single small lesion had developed in a tooth of one immunised animal, while the other remains caries-free.

a. IMMUNOGENICITY OF PURE ANTIGEN A

Figure 2:
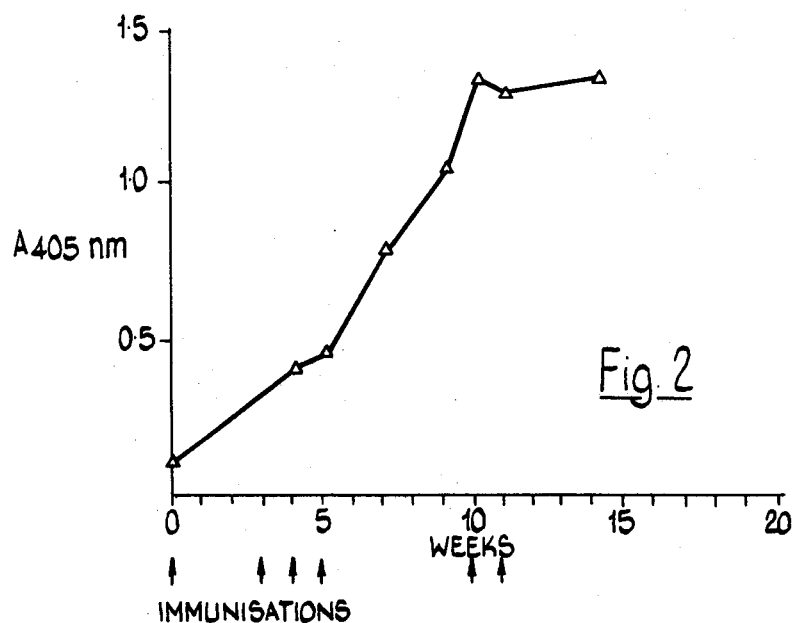
FIG. 2 shows IgG responses to antigen A in a single animal.

It is clear from the above results that antigens A and B injected as components of whole bacteria or bacterial cell walls are capable of eliciting an immune response when no adjuvant is present (group C) or when aluminium hydroxide adjuvant is added (group 11). Immunisation with the pure antigens however, requires the presence of adjuvant for a rapid and sustained response. Responses of a single monkey (about 5 kg body weight) immunised with 50 µg of antigen A (prepared as described above using ammonium sulphate precipitation) with aluminium hydroxide is illustrated in FIG. 2.

b. IMMUNOGENICITY OF PURE ANTIGEN A

Two groups of Macaca fascicularis monkeys were kept under the general conditions of caging, diet and handling described by W. H. Bowen et al., Br.dent.J., 1975, 139,45.

Experiment 1 consisted of four animals born in captivity in the UK (their mothers having been captured in the wild of SE Asia while pregnant). At the start of the experiment the two control animals were one male aged 18 m and weighing 1.26 kg and one female (17 m, 1.32 kg), while the two animals which were to be immunised were also one male (14 m, 1.60 g) and one female (20 m, 1.59 kg). All animals had a fully erupted deciduous dentition. The first permanent molar teeth started to erupt within a few months of commencing the experiment.

Experiment 2 consisted of nine animals newly imported (to the UK) from the wild. These were divided into two groups matched as closely as possible for sex, weight and dental development. The contrl group mean weight was 1.52±0.29 kg and the group to be immunised with antigen A mean weight was 1.55±0.55 kg. Each group had equal numbers of males and females, with an additional female in the control group.

The antigen used for immunisation was antigen A prepared from S.mutans strain Ingbritt. In the early stages of experiments 1 and 2 the antigens were purified from culture filtrates by conventional biochemical procedures of fractional precipitation with ammonium sulphate and column chromatography (Example 1a above), but later these methods were replaced by the purification of a column prepared with monospecific rabbit antiserum to antigen A (Example 1b or 1c above). Purity of antigen preparations was monitored by SDS—polyacrylamide gel electrophoresis and crossed immunoelectrophoresis against polyvalent antisera, particular attention being paid to the possibility of contamination with glucan-binding proteins and lipoteichoic acid.

For immunisation, monkeys were injected with 50–100 µg doses of protein in sterile saline with 10% aluminium hydroxide adjuvant at two subcutaneous sites on the lower limbs. In experiment 1 injections took place after 0, 1, 1½, 2, 2½, 6, 13, 20 and 26 months. In experiment 2 injections took place after 0, 1, 2, 5, 10, 16½ and 23 months.

Serum IgG antibody levels to antigen A were assayed by enzyme linked immunosorbent assay (ELISA) in microtitration trays.

Antigen A was found to be a good immunogen and a strong immune response was observed immediately following the first few injections. This was well sustained between booster injections. The kinetics of the response indicate that adequate antibody levels could be attained by a much simpler immunisation schedule than that used for experiments 1 and 2 and the multiple injections were only employed because the immunogenicity of the antigen could not be predicted.

Both of the control animals in experiment 1 developed carious lesions in their deciduous teeth, one animal having 8 lesions and the other a total of 9. A high level of caries was also observed in the permanent teeth (Table 2). In striking contrast, no carious lesions were found in the deciduous teeth of either of the immunised animals and in the permanent teeth one immunised monkey had only a single carious lesion after 30 months consuming a sugar rich diet, while the other had 2 such lesions, (Table 2).

Experiment 2 confirmed the finding that immunisation with antigen A conferred protection against caries as 3 out of 4 immunised animals had a caries free permanent dentition while one had a single lesion at a stage of the experiment when all of the matched controls had caries with a mean score of 3.6, (Table 2).

It has therefore been shown, in two independent experimental groups of monkeys, that immunisation with antigen A can reduce caries in both deciduous and permanent teeth by approximately 90%.

TABLE 2

| | Experiment 1. | |
|---|---|---|
| Time after first injection | Mean caries score (± SD) in permanent teeth | |
| | Control (2) | Immunised (2) |
| 9 months | 1.5 ± 0.7 | 0 |
| 11 | 4.0 ± 1.4 | 0 |
| 13 | 8.0 ± 1.4 | 0 |
| 16 | 8.0 ± 0 | 0.5 ± 0.7 |
| 18 | 8.5 ± 0.7 | 0.5 ± 0.7 |
| 21 | 8.8 ± 0.7 | 0.5 ± 0.7 |
| 25 | 8.5 ± 0.7 | 1.5 ± 0.7 |
| 27 | 9.5 ± 2.1 | 1.5 ± 0.7 |
| 30 | 12.0 ± 4.2 | 1.5 ± 0.7 |

| | Experiment 2 | |
|---|---|---|
| Time after first injection | Mean caries score (±SD) in permanent teeth | |
| | Control (5) | Immunised (4) |
| 7 months | 0 | 0 |
| 9 | 0.8 ± 1.1 | 0 |
| 11 | 0.8 ± 1.8 | 0 |

TABLE 2-continued

| | | |
|---|---|---|
| 14 | 2.0 ± 0.7 | 0.25 ± 0.5 |
| 19 | 2.6 ± 1.1 | 0.25 ± 0.5 |
| 23 | 3.8 ± 1.8 | 0 |
| 25 | 3.6 ± 1.1 | 0.25 ± 0.5 |

We claim:

1. A process for preparing an antigen preparation from bacteria of the species *Streptococcus mutans* comprising growing bacteria of the species *S mutans* in a culture medium to produce a cell culture, removing at least the cell walls from said cell culture to leave a protein solution, and separating the antigen preparation from the protein solution by a method of separation which comprises contacting the protein solution with an immobilized antibody, washing unwanted materials from the immobilized antibody and eluting the antigen preparation from the immobilized antibody, wherein the immobilized antibody has a specificity for one or more antigenic proteins which are selected from the group consisting of:

(A) proteins which are present on the cell walls of *Streptococcus mutans* genetic group I, are not extractable from said walls by boiling with 10 g/liter sodium dodecyl sulphate for 20 minutes, have a molecular weight of about 29,000, have an isoelectric point of about 4.1 to 4.5, on treatment with a proteolytic enzyme form no precipitin lines when tested by immunodiffusion against antiserum to sodium dodecyl sulphate extracted cells of *Streptococcus mutans* and do not cross-react with heart tissue; and (B) proteins which react serologically with antibodies to proteins of group member A.

2. A process according to claim 1 wherein the bacteria is a strain of *S mutans* genetic group I.

3. A process according to claim 2 wherein the bacteria is a strain of serotype c.

4. A process according to claim 1 wherein the immobilised antibody has a specificity for one or more antigenic proteins which are present on the cell walls of *Streptococcus mutans* genetic group I, are not extractable from said walls by boiling with 10 g/liter sodium dodecyl sulphate for 20 minutes, have a molecular weight of about 29,000, have an isoelectric point of about 4.1 to 4.5, on treatment with a proteolytic enzyme form no precipitin lines when tested by immunodiffusion against antiserum to sodium dodecyl sulphate extracted cells of *Streptococcus mutans* and do not cross-react with heart tissue.

* * * * *